United States Patent [19]

Ryan

[11] Patent Number: 5,008,201
[45] Date of Patent: Apr. 16, 1991

[54] SIMULATED HUMAN PLATELETS FROM RED BLOOD CELLS

[75] Inventor: Wayne L. Ryan, Omaha, Nebr.

[73] Assignee: Streck Laboratories, Inc., Omaha, Nebr.

[21] Appl. No.: 527,828

[22] Filed: May 24, 1990

[51] Int. Cl.$^5$ .................. G01N 31/00; G01N 33/48
[52] U.S. Cl. .......................................... 436/10; 436/11; 435/2
[58] Field of Search ....................... 436/8–18; 435/2; 252/408.1; 424/3; 356/243

[56] References Cited

U.S. PATENT DOCUMENTS

| 4,412,004 | 10/1983 | Ornstein et al. | 436/10 |
| 4,436,821 | 3/1984 | Ryan | 436/11 |
| 4,698,312 | 10/1987 | Wong et al. | 436/10 |
| 4,777,139 | 10/1988 | Wong et al. | 436/10 |

Primary Examiner—Thomas Wallen
Attorney, Agent, or Firm—Larson and Taylor

[57] ABSTRACT

Lysable, blood platelet controls are prepared by treating animal red blood cells larger than or within the size range of human blood platelets with a fixing agent for red blood cells for a time sufficient to partially rigidify the red blood cell membrane enabling shrinking to a permanently shrunk condition, subjecting distinct groups of said partially fixed red blood cells to hemolysis wiht a hemolytic agent to partially remove hemoglobin therefrom, the hemolysis of each distinct group of cells removing a different amount of hemoglobin, subjecting the resulting red blood cells to centrifugation to collapse the red blood cell membrane around the hemoglobin remaining in said cells, said distinct group of cells and the extent of hemolysis being selected so as to provide after said centrifugation a mixture of permanently shrunken lysable cells that simulate in number, size and volume distribution the platelets present in human whole blood.

5 Claims, No Drawings

SIMULATED HUMAN PLATELETS FROM RED BLOOD CELLS

BACKGROUND OF THE INVENTION

1. Field of the Invention

This invention relates to the preparation of a lysable blood platelet reference control for use in a number of routine hematologic determinations. More particularly, the invention is directed to lysable, blood platelet reference controls prepared from animal red blood cells.

2. State of the Art

Stabilized human platelets are commonly used as reference controls for checking the performance characteristics of blood particle counting instruments. The use of human platelets for this purpose, however, is not without its limitations. For example, human platelets are difficult to handle since they are easily activated and tend to aggregate. Human platelets are also very expensive.

Yet another shortcoming of stabilized human platelet reference controls has been experienced with multi-parameter reference controls which contain red blood cells and white blood cells as well as the platelets. In such multi-parameter reference controls, the red blood cells and the platelets mix at different rates, the red blood cells mixing more rapidly, and consequently, it is not uncommon to experience erratic platelet counts when the multi-parameter controls must be resuspended after days of settling.

It is not surprising, therefore, particularly with the advent of automated devices capable of performing multiple hemotogical determinations, to find a growing need for less expensive substitutes useful as blood platelet reference controls. Robert A. Hunt U.S. Pat. No. 4,179,398 describes a blood platelet reference control prepared by shrinking goat red blood cells to the size of human blood platelets and then fixing the shrunken goat blood cells to stabilize them. The shortcoming of the platelet control composition of U.S. Pat. No. 4,179,398 is that the cells shrunken by hypertonic solution as described in the patent tend to return to their original shape. In other words, simulated platelets prepared by U.S. Pat. No. 4,179,398 when put into an isotonic solution often return to their original shape thereby resulting in an inaccurate count.

Another drawback of the platelet control composition of U.S. Pat. No. 4,179,398 resides in the fact the size of the simulated platelets prepared is only the general size of human blood platelets and not the size distribution of human blood platelets. Any system for automated platelet counting which distinguishes human platelets from other cells in the blood on the basis of the characteristic size range and volume distribution of platelets requires that the reference control material closely simulate the size range and volume distribution characteristics of platelets in normal human blood.

Chastain, Jr. et al U.S. Pat. No. 4,264,470 recognizes the problem associated with reference controls of the type aforementioned which do not closely simulate the size range and volume distribution characteristics of platelets in normal human blood and proposes a method for obtaining goat blood cells with the desired size and volume distributions by using different goats, inducing anemia in goats, etc., determining the number and size distribution of the red blood cells in the various samples thus obtained and then blending the red blood cells to gain the appropriate size and volume distributions. The multiple steps and controls necessary to such a prior art process renders it unduly difficult and cumbersome.

Another disadvantage in prior art reference controls for use in blood platelet controls resides in the fact that they are "fixed" or stabilized. When "fixed" platelets are used in multi-parameter controls containing red blood cells, white blood cells and platelets, the platelets may add to the white cell count because "fixed" platelets do not lyse or fragment. Consequently, when a white blood cell count is taken, some of the large platelets are counted in the white blood cell channels giving an inaccurate total white blood cell count.

Wayne Ryan U.S. Pat. No. 4,436,821 describes lysable, permanently shrunk blood platelet reference controls and methods for their preparation; which controls do not return to their original shape when placed in an isotonic solution and closely simulate the size range and volume distribution characteristics of platelets in normal human blood. According to the method of this patent the reference controls are obtained by first fixing animal red blood cells larger than or within the size range of human blood platelets with a fixing agent for red blood cells to partially rigidify the membrane of the cells and then subjecting distinct groups of the partially fixed cells to different osmotic pressures to permanently shrink the cells and provide a mixture that simulates in size, number and volume distribution blood platelets present in human whole blood.

The present invention provides an alternative method of obtaining these lysable blood platelet reference controls described in U.S. Pat. No. 4,436,821.

SUMMARY OF THE INVENTION

In accordance with the present invention, lysable blood platelet reference controls are obtained by a method comprising treating animal red blood cells larger than or within the size range of human blood platelets with a fixing agent for red blood cells for a time sufficient to partially rigidify the red blood cell membrane enabling shrinking to a permanently shrunk condition, subjecting distinct groups of said partially fixed red blood cells to hemolysis with a hemolytic agent to partially remove hemoglobin therefrom, the hemolysis of each distinct group of cells removing different amounts of hemoglobin, and subjecting the resulting red blood cells to centrifugation to collapse the red cell membrane around the hemoglobin remaining in said cells, said distinct groups of cells and the extent of hemolysis being selected so as to provide after said centrifugation a mixture of permanently shrunken, lysable cells that simulate in number, size and volume distribution the platelets present in human blood.

DETAILED DESCRIPTION OF THE INVENTION

The red blood cells from which the lysable platelet reference controls of the present invention are prepared can be suitable animal red blood cells. It is only necessary that the starting red blood cells from the animal species be larger in size or within the size range of the human blood platelets (approximately 2-40u$^3$) and shrinking the cells to a point where they fall within the approximate size of the platelets of human blood. Thus, there is no need for a particular species of red blood cell. In general, however, the arting red blood cells will have a mean cell volume of about 25 to 55u$^3$. Illustrative of suitable red blood cells are those from the blood of goats, sheep, pigs, cows, cats and the like.

Pursuant to the method of the present invention, whole blood from a donor animal is collected and mixed with an anticoagulant and the plasma and red blood cells are separated from the blood by any of the conventional methods such as centrifugation or settling. The anticoagulant may be sodium citrate, ammonium oxalate, potassium oxalate, or any other conventional anticoagulant which will not have an adverse effect on the red blood cells. The separated red blood cells are then washed free of all plasma, anticoagulant and other blood particles and suspended in a suspension medium nondeleterious to the red blood cells. The suspension medium is preferably a physiological salt solution such as an isotonic saline solution advantageously buffered to a pH neutral to alkaline, preferably a pH of 7 to 9. Preferred buffering agents include the alkali metal phosphates such as disodium phosphate, monopotassium phosphate, monosodium phosphate, sodium bicarbonate and the like and mixtures thereof. In general, suspensions of up to 50% by volume, preferably about 10 to 30% by volume red blood cells are prepared.

Next, the elasticity of the red cell membrane is decreased, that is, the red cell membrane is partially rigidified by treating the red blood cells in suspension with a fixing agent. Fixing agents for red blood cells are well known to those of ordinary skill in the art and include, for instance, aldehydes, such as formaldehyde and glutaraldehyde, tannic acid or other chemical fixative agents. The amount of fixing agent added to the suspension of red blood cells will vary depending upon the particular species of red blood cells employed, the number of cells in the suspension being treated, the fixing agent employed and the counting instrument that is to be checked by the reference control. In the case of aldehyde fixing agents, the concentration will usually vary from 0.004 to 0.10% by weight per $1 \times 10_6/mm^3$ of red blood cells. With glutaraldehyde and sheep red blood cells a concentration of glutaraldehyde about 0.01 to 0.02% per $10^6$ cells is preferred. When goat red blood cells are used, a concentration of about 0.004 to 0.015% glutaraldehyde per $10_6$ cells is preferred.

In all cases, the reaction of the fixing agent with the red blood cells is allowed to proceed until they are partially rigidified. By the term "partially rigidified" as used herein and in the appended claims is meant a degree of rigidification that enables subsequent shrinking of the red blood cells to a permanently shrunk condition. Usually this degree of rigidification falls in the range of 10 to 50% of complete rigidification for the red blood cells employed. Ordinarily the fixing period necessary to achieve the desired degree of rigidification comprises about 4 to 24 hours.

After the red blood cells have been partially rigidified, suspensions thereof are divided into a plurality of distinct groups or lots and each group is subjected to a partial hydrolysis designed to remove a predetermined amount of hemoglobin from the cells in each group which amount differs from the amounts removed from the other groups. Since each group of cells contains different amounts of residual hemoglobin, when the cells are subsequently subjected to centrifugation to collapse and shink the cell membrane around the residual hemoglobin, the resulting family of shrunken red cells in each group will be of a different size. Thus, the amount of hemoglobin remaining in a cell determines the actual size of the ultimate platelet. The apparent size, however, depends on the method of measurement. In instruments using lasers, (e.g., Technicon H-1 and Ortho ELT-8) the residual hemoglobin in the cell determines the apparent size while in instruments measuring platelets size by impedence, the size is determined by the membrane. Therefore, if the control is to work on all types of instruments, both the hemoglobin content and the size of cell must be adjusted.

The amount of residual hemoglobin that remains in a red blood cell is primarily dependent on the amount of fixative which determines the degree of rigidity of the membrane and the particular hemolysis procedure employed. As aforementioned, the rigidity of the cell membrane is a function of the fixing agent concentration relative to the red cell concentration. In other words, the amount of fixing agent must be adjusted relative to the red blood cell number so as to not only provide a partially fixed red cell membrane which is shrinkable upon centrifugation but also allow for the desired degree of partial hemolysis. The range of concentrations of fixing agent per $1 \times 10_6/mm^3$ of red blood set forth above normally achieves this result.

The concentration of hemolytic agent used in the hemolysis step of the invention may vary depending upon the particular hemolytic agent employed but in all instances will be sufficient to carry out the desired partial hemolysis. Ordinarily, concentrations of hemolytic agents in the range of about 0.001 to 0.1 grams per liter of water have proved to be effective. Also, any of the hemolytic agents (including hemolysins) well known in the art and commonly employed in hemolysis procedures are contemplated. A preferred hemolytic agent is ACT (an aqueous solution of ammonium chloride and tris(hydroxymethyl)aminomethane).

The hemolysis can be carried out by simply suspending the partially fixed red cells in the solution hemolytic agent until the residual hemoglobin content of the cells reaches a predetermined level. The latter can be determined by any suitable means known to those skilled in the art as, for instance, by monitoring the progress of hemoglobin lysis by use of an Ortho ELT-8 laser which records size based on the amount of hemoglobin remaining. When the desired residual hemoglobin content is reached, the cells are removed from the solution of hemolytic agent and washed prior to being permanently shrunk by centrifugation.

The shrinking step is conducted by subjecting the partially fixed, partially hemolyzed animal red blood cells to a centrifugation sufficient in terms of time and revolutions per minute to cause collapse of the cell membrane around the hemoglobin remaining in the partially hemolyzed red blood cells. Centrifugating at 1000 to 1500 rpm for 20 to 50 minutes is usually satisfactory. (Relative centrifugal force of 300–700.)

When the centrifuging is finished, the permanently shrunk cells are separated and washed. The groups or lots of washed and permanently shrunk red blood cells are then blended to produce a mixture of permanently shrunken cells that simulate in number, size and volume distribution the platelets in human whole blood.

The reference control compositions of the invention may also include other addenda conventionally added to such compositions. Illustrative of additives that can be included are bactericidal agents and antifungal agents such as neomycin and methylparaben.

The following examples are given by way of illustration and are not to be construed as limiting the invention, many variations of which are possible without departing from the spirit or scope thereof.

EXAMPLE

Goat blood is collected in a citrate anticoagulant and the blood is centrifuged to remove the plasma. The red blood cells are washed with isotonic phosphate buffered saline to remove all plasma and anticoagulant.

The goat cells are counted and the concentration of goat cells adjusted to $8.0 \times 10^6$/ul by addition of phosphate buffered saline having a pH of 7.4. Gluteraldehyde (25%) is then slowly added to the cells with mixing until a final concentration of 0.016% glutaraldehyde is provided. The reaction is allowed to proceed overnight at 6° C. The next day the resulting partially rigidified red blood cells are divided into three lots A, B and C. The cells of lots A, B and C are then separately resuspended into three hemolytic ACT solutions prepared and the hemolysis started. The ACT solutions are made from 75 g/l ammonium chloride and 20.59 g/l trisbuffer (i.e. tri(hydroxymethyl) aminomethane) by adding one part of the trisbuffer to 9 parts of ammonium chloride and adding distilled water to provide a final concentration per liter of 2.1 gm trisbuffer and 6.75 gm ammonium chloride. The progress of the lysis in each solution is followed on an Ortho ELT-8 laser and the cells are removed from the solution as the laser records the size of the developing platelet by measuring the residual hemoglobin.

The partially hemolyzed red cells thus prepared are washed and separately subjected to centrifugation at 1200 rpm for 15 minutes and the supernatant removed.

The resulting cells are washed and one volume of each of the three lots are blended to produce a log normal curve resembling human platelets. The reference control thus prepared is found to be readable by all of the following counting instruments: H-1 Technicon, ELT-800, Sequoia-Turner Cell Dyn 200, S+IV Coulter and Sysmex E.

I claim:

1. A method of preparing lysable, blood platelet reference control comprising treating animal red blood cells larger than or within the size range of human blood platelets with a fixing agent for red blood cells for a time sufficient to partially rigidify the red blood cell membrane enabling dividing said shrunk red blood cells into distinct groups and shrinking to a permanently shrunk condition, subjecting said distinct groups of said partially fixed red blood cells to hemolysis with a hemolytic agent to partially remove hemoglobin therefrom, the hemolysis of each distinct group of cells removing a different amount of hemoglobin, subjecting the resulting red blood cells to centrifugation to collapse the red blood cell membrane around the hemoglobin remaining in said cells, said distinct group of cells and the extent of hemolysis being selected so as to provide after said centrifugation a mixture of permanently shrunken lysable cells that simulate in number, size and volume distribution the platelets present in human whole blood.

2. A method according to claim 1 wherein the fixing agent is aldehyde.

3. A method according to claim 2 wherein the aldehyde is glutaraldehyde.

4. A method according to claim 1 wherein the hemolytic agent is an aqueous solution of ammonium chloride and tris(hydroxymethyl)aminomethane.

5. A method according to claim 1 wherein the animal red blood cells are goat red blood cells.

* * * * *